US010369323B2

(12) United States Patent
Joseph

(10) Patent No.: US 10,369,323 B2
(45) Date of Patent: Aug. 6, 2019

(54) SONIFICATION OF BIOMETRIC DATA, STATE-SONGS GENERATION, BIOLOGICAL SIMULATION MODELLING, AND ARTIFICIAL INTELLIGENCE

(71) Applicant: Robert Mitchell Joseph, Petaluma, CA (US)

(72) Inventor: Robert Mitchell Joseph, Petaluma, CA (US)

(\*) Notice: Subject to any disclaimer, the term of this patent is extended or adjusted under 35 U.S.C. 154(b) by 72 days.

(21) Appl. No.: 15/642,691

(22) Filed: Jul. 6, 2017

(65) Prior Publication Data

US 2017/0326331 A1 Nov. 16, 2017

Related U.S. Application Data

(63) Continuation-in-part of application No. 15/405,744, filed on Jan. 13, 2017, now abandoned.
(Continued)

(51) Int. Cl.
*A61M 21/00* (2006.01)
*A61B 5/00* (2006.01)
(Continued)

(52) U.S. Cl.
CPC .............. *A61M 21/00* (2013.01); *A61B 5/486* (2013.01); *A61M 21/02* (2013.01); *G06N 3/08* (2013.01);
(Continued)

(58) Field of Classification Search
CPC A61M 21/00; A61M 2021/0027; G06N 3/08; A61B 5/486; A61B 5/0482; G16H 50/20; G06F 19/00
(Continued)

(56) References Cited

U.S. PATENT DOCUMENTS 9,440,657 B1* 9/2016 Fields .................. B60K 28/066
2006/0029912 A1* 2/2006 Kearby ..................... G09B 5/04
434/116
(Continued)

OTHER PUBLICATIONS

International Search Report and Written Opinion for PCT/US2018/038522 dated Sep. 11, 2018, 10 pages.
(Continued)

*Primary Examiner* — Navin Natnithithadha
*Assistant Examiner* — Sunita Reddy
(74) *Attorney, Agent, or Firm* — Workman Nydegger

(57) ABSTRACT

Embodiments are generally directed to methods, systems and devices for generating and playing back a personalized state song representing a target state of a user. In one scenario, a computer system accesses biometric data corresponding to various bodily systems of a user. The computer system encodes the biometric data into data structures that are configured for modeling using an algorithm that is specific to the user. The computer system models the encoded biometric data to identify specified patterns in the encoded biometric data, and these identified patterns are used to generate a personalized algorithm that corresponds with the identified patterns unique to the user. The computer system then synthesizes a state song using the personalized algorithm, which represents a specific biometric state for one of the bodily systems, and plays back the state song to the user to induce the user to the specific biometric state.

20 Claims, 14 Drawing Sheets

Related U.S. Application Data

(60) Provisional application No. 62/388,076, filed on Jan. 15, 2016.

(51) Int. Cl.
  G06N 3/08 (2006.01)
  G16H 50/20 (2018.01)
  A61M 21/02 (2006.01)

(52) U.S. Cl.
  CPC ..... G16H 50/20 (2018.01); *A61M 2021/0027* (2013.01)

(58) Field of Classification Search
  USPC ..................................................... 600/26–28
  See application file for complete search history.

(56) References Cited

U.S. PATENT DOCUMENTS

| | | | | |
|---|---|---|---|---|
| 2008/0214944 A1* | 9/2008 | Morris | ................... | G06F 19/00 600/509 |
| 2008/0319252 A1* | 12/2008 | Chapman | .............. | A61M 21/02 600/27 |
| 2009/0000463 A1 | 1/2009 | Childs, Jr. et al. | | |
| 2011/0115626 A1* | 5/2011 | Goldstein | ............... | H04S 1/005 340/540 |
| 2011/0270052 A1* | 11/2011 | Jensen | ................. | A61B 5/0002 600/302 |
| 2012/0116176 A1* | 5/2012 | Moravec | .............. | A61B 5/6898 600/300 |
| 2012/0198985 A1 | 8/2012 | Ludwig | | |
| 2013/0131537 A1* | 5/2013 | Tam | ..................... | A61B 5/4854 600/544 |
| 2014/0278220 A1 | 9/2014 | Yuen | | |
| 2014/0307878 A1* | 10/2014 | Osborne | ........... | G06F 17/30743 381/56 |
| 2015/0133749 A1 | 5/2015 | Janata et al. | | |
| 2015/0213789 A1 | 7/2015 | Plott et al. | | |
| 2015/0297109 A1 | 10/2015 | Garten et al. | | |
| 2015/0306136 A1* | 10/2015 | Meloni | ................. | A61K 33/00 424/600 |
| 2015/0313496 A1* | 11/2015 | Connor | ................ | A61B 5/0476 600/301 |
| 2016/0086500 A1 | 3/2016 | Kaleal, III | | |
| 2016/0270656 A1* | 9/2016 | Samec | ................... | A61B 3/085 |

OTHER PUBLICATIONS

Office Action in U.S. Appl. No. 15/405,744 dated Jul. 12, 2018, 14 pages.

* cited by examiner

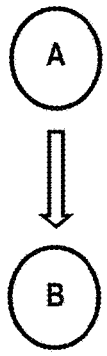
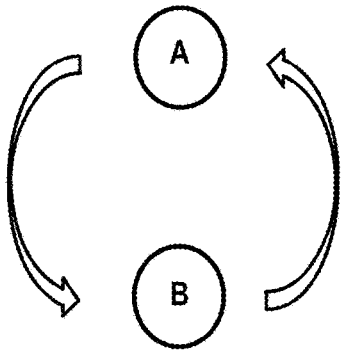
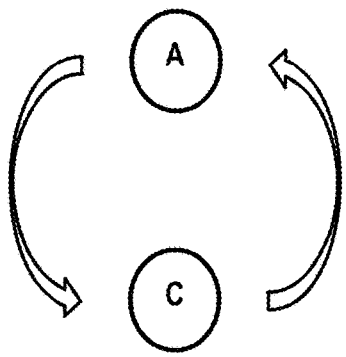
Fig. 1　　　　　　Fig. 2　　　　　　Fig. 3
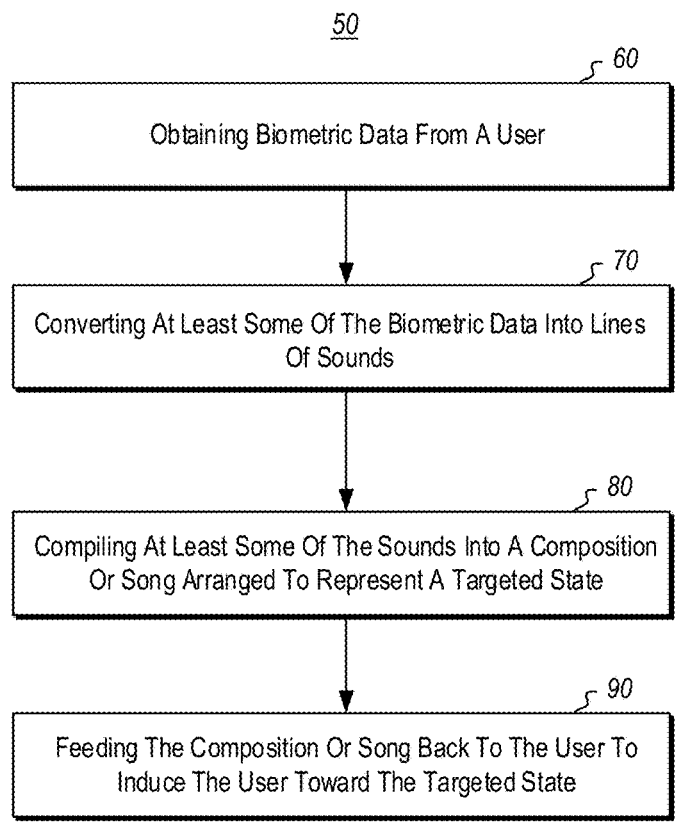
Fig. 4

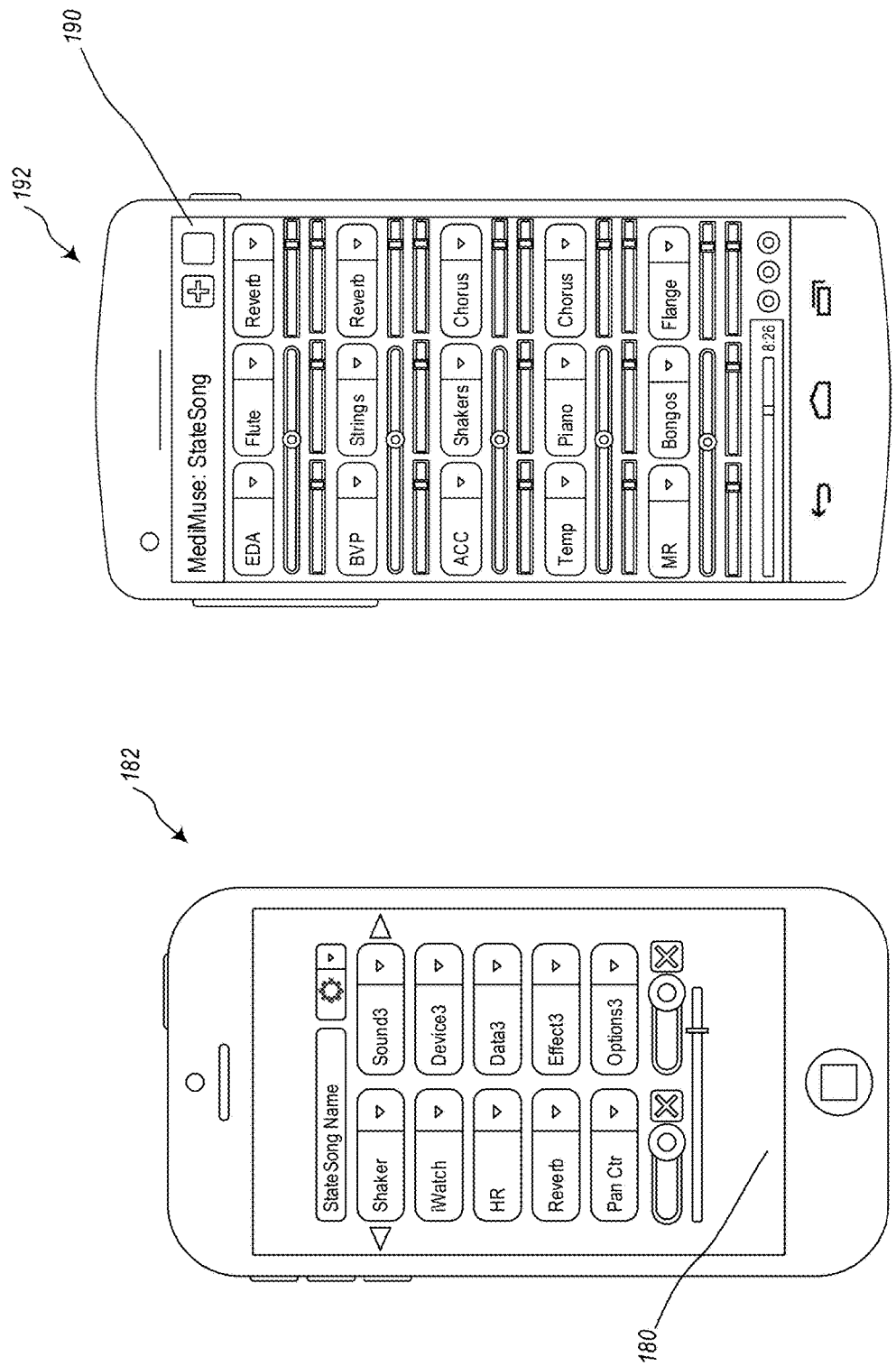

SONIFICATION OF BIOMETRIC DATA, STATE-SONGS GENERATION, BIOLOGICAL SIMULATION MODELLING, AND ARTIFICIAL INTELLIGENCE

CROSS-REFERENCE TO RELATED APPLICATIONS

This CIP application claims the benefit of, and priority to, U.S. patent application Ser. No. 15/405,744, entitled "SONIFICATION OF BIOMETRIC DATA STATE-SONGS GENERATION, BIOLOGICAL STIMULATION MODELLING AND ARTIFICIAL INTELLIGENCE," filed on Jan. 13, 2017, which application claims priority to and the benefit of U.S. Provisional Patent Application Ser. No. 62/388,076, entitled "SONIFICATION OF BIOMETRIC DATA STATE-SONGS GENERATION, BIOLOGICAL STIMULATION MODELLING AND ARTIFICIAL INTELLIGENCE," and filed on Jan. 15, 2016, both of which applications are incorporated by reference herein in their entirety.

BACKGROUND

An individual's "states" (i.e., happy, depressed, fearful) embody "state dependent behaviors" (smiling, inactivity, lashing out). By examples: persons suffering from PTSD are suspended in a state of trauma, and within that traumatized state, a set of negatively reactive behaviors are expressed. Outside of the traumatized state, the set of PTSD behaviors are less accessible. More positively, behaviors related to a calm state generally exclude the actions associated with trauma, stress and anxiety. Ideally, one would be able control his/her emotions so as to achieve positive states and sustain constructive behaviors. Unfortunately, the control of one's states can be elusive.

There is thus a need for systems and methods for more effectively controlling state dependent behaviors of individuals.

BRIEF DESCRIPTION OF THE DRAWINGS

These and other features, aspects, and advantages of the present disclosure will become better understood regarding the following description, appended claims, and accompanying drawings.

FIGS. 1-3 illustrate different external and internal states for context.

FIG. 4 illustrates a method for controlling state dependent behaviors of a user according to an embodiment.

FIG. 12 illustrates a user interface according to an embodiment.

FIG. 13 illustrates a user interface according to another embodiment.

BRIEF SUMMARY

Figure 5:
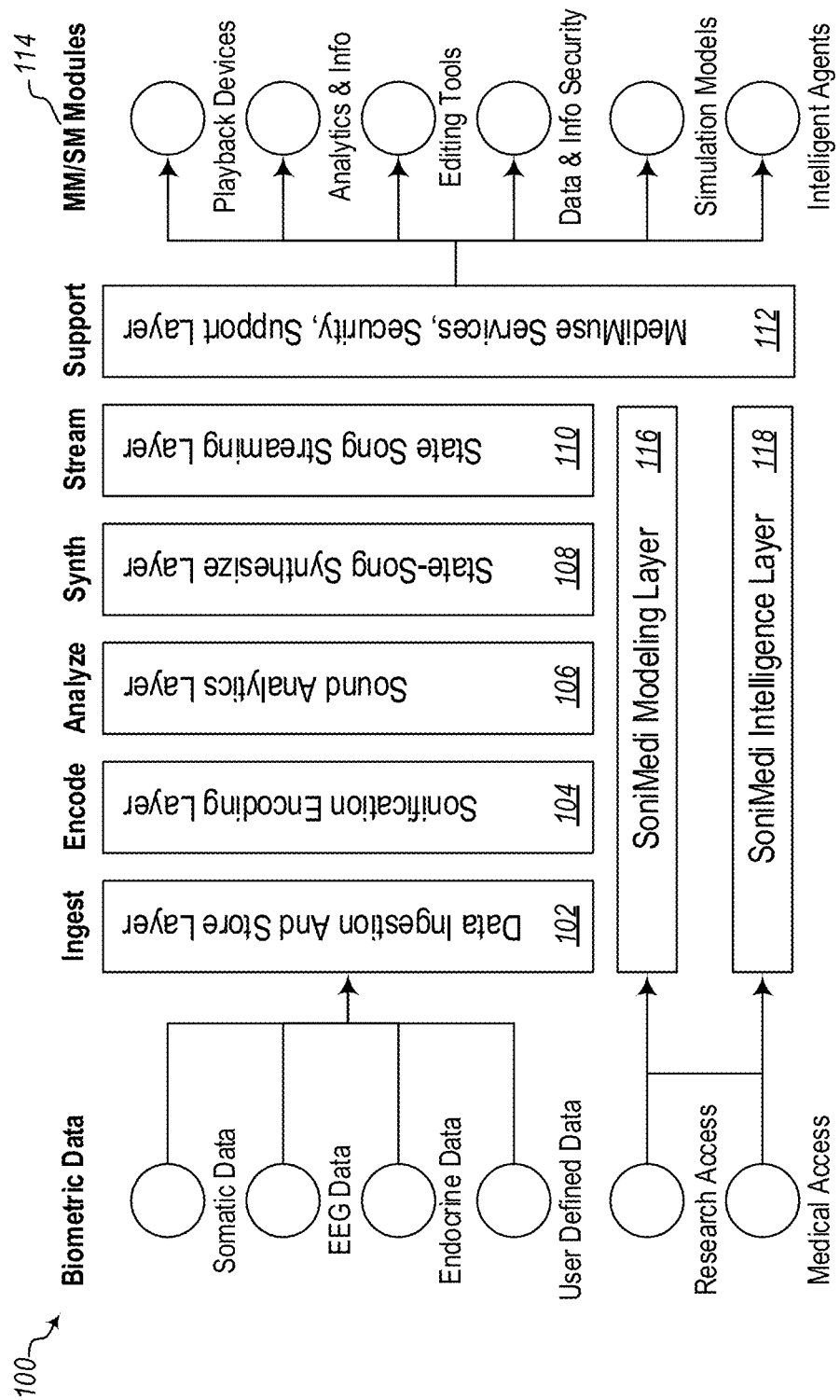
FIG. 5 illustrates a system for controlling state dependent behaviors of a user according to an embodiment

Embodiments described herein are generally directed to methods, systems and devices for generating and playing back a personalized state song representing a target state of a user. For example, in one embodiment, a computer system accesses biometric data corresponding to various bodily systems of a user. The computer system encodes the biometric data into data structures that are configured for modeling using an algorithm that is specific to the user. The computer system models the encoded biometric data to identify specified patterns in the encoded biometric data, and these identified patterns are used to generate a personalized algorithm that corresponds with the identified patterns unique to the user. The computer system then synthesizes a state song using the personalized algorithm, which represents a specific biometric state for one of the bodily systems, and plays back the state song to the user to induce the user to the specific biometric state.

DETAILED DESCRIPTION OF VARIOUS EMBODIMENTS

A better understanding of different embodiments of the disclosure may be had from the following description read with the accompanying drawings.

While the disclosure is susceptible to various modifications and alternative constructions, certain illustrative embodiments are in the drawings and are described below. It should be understood, however, there is no intention to limit the disclosure to the specific embodiments disclosed, but on the contrary, the intention covers all modifications, alternative constructions, combinations, and equivalents falling within the spirit and scope of the disclosure.

It will be understood that unless a term is expressly defined in this application to possess a described meaning, there is no intent to limit the meaning of such term, either expressly or indirectly, beyond its plain or ordinary meaning.

Any element in a claim that does not explicitly state "means for" performing a specified function, or "step for" performing a specific function is not to be interpreted as a "means" or "step" clause as specified in 35 U.S.C. § 112(f).

Embodiments of the present disclosure transform biometric data from a user into sound which is fed back into the user to beneficially influence state dependent behaviors of the user. For instance, methods of the present disclosure can involve generating biometric based music to induce a desired or target internal state of clam, learning, and/or second wind in the user. Alternatively, methods described herein can involve generating biometric based music for use in a movie or television soundtrack to induce one or more desired audience emotions. In other embodiments, methods of the present disclosure can be adapted to provide an alternative mode and methodology for biological stimulation modelling. In yet other embodiments, methods of the present disclosure can be adapted to generate biometric based music and utilize the same as a predictive, diagnostic, and/or artificial intelligence tool as described in more detail below.

FIGS. 1-3 illustrates exemplary relationships between internal and external states of a user to provide context to the present disclosure. Referring to FIG. 1, an internal state A comprises the physiological state of depressed, and an external state B comprises a physical posture B, which when depressed, includes slumped shoulders, chin pointing down, low effect. Internal state A of depressed and the physical posture B are generally isomorphic or two different presentations of the same state at different levels, internal and external. The physical posture B is generally a result of the individual's internal state or physiology. For instance, if the internal physiology is depressed the posture physical presents as such.

Referring to FIG. 2, the relationship between the internal state A and external state or physical posture B can be reciprocal in that the physical posture B feeds back upon and impacts the internal state A in such a way that if we change the physical posture B by pulling the shoulders back, pushing the chin upwards and projecting a posture of confidence, the internal state A conforms in accordance with the physical posture B of confidence to change to an internal state of confidence. In other words, the internal state A creates the physical posture B but the physical posture B can influence or force the internal state A to conform to the physical posture B. Thus, while the external state or physical posture B is a postural isomorph derived from within the internal or physiological state A, the external state or physical posture B can control the internal state A from the outside-in. Cybernetics dictates that if the external state B is fed back into the system of the internal state A from which it was derived, the internal state A will at least in part conform to the external state B.

Referring to FIG. 3, the described relationship between the internal state A and the external state or physical posture B can be extended to include other isomorphs such as a sonic isomorph. Biometric based music can be derived from a system in an internal state A and then fed back into the system to influence the system. The biometric based music can be referred to as a state-song C. This state-song C represents a state of a system of origin and can cause the internal state A of that system to at least in part conform to the state-song C. For instance, if that state-song C is generated from biometric data obtained from a user with an elevated heart rate that user can listen to the state-song C at a different time when the user's heart rate is reduced and experience a palpable increase in its heart rate.

Systems and methods of the present disclosure can advantageously thus generate biometric based music from biometric or physiological data to create a sonic isomorph of a state that induces that same or similar state. This can be identified as a phenomenological isomorph meaning that the same result can be achieved with other state isomporphs (e.g., music). Similar to the previous example of the physiology/posture case, the state-song C derived from a specific internal state can be fed back into an user or system of origin to induce a targeted state; such as calm, aware, excitement, second wind, focus, etc.

Systems and methods of the present disclosure can be adapted to address PTSD, depression, anxiety, insomnia, and/or any other internal state so as to modify the physiology and behaviors that are encumbered by those states. Other embodiments, can be adapted to produce individualized sonic simulation models that merge somatic, EEG and endocrinological data. Alternatively, such personalized simulation models can be used by artificial intelligent agents for health diagnostics and interventions.

FIG. 4 illustrates exemplary steps in a method 50 for controlling state dependent behaviors of a user. In an act 60, biometric data is obtained from a user. The biometric data can include somatic data, endocrine data, cortical data, or any other suitable biometric data.

In an act 70, at least some of the biometric data is converted or transformed into lines of sound. This may be referred to as "sonifying" the biometric data. Conversion or transformation of the biometric data may include frequency/amplitude conversion and/or algorithmic processing. The conversion and/or transformation of the biometric data can be performed by one or more modules as discussed below. For instance, the biometric data can be converted or transformed into lines of sound by a processing module of a computing device.

In an act 80, at least some of the lines of sound are compiled into compositions or state-songs arranged to represent a targeted state of the user. The conversion and/or transformation of the biometric data can be performed by one or more modules as discussed below. The targeted states can include different states such as calm, learning, exercise, rest, etc.

In an act 90, the compilation or state-song is fed or provided back to the user to induce the user to the targeted state. The compilation or state-song can be fed or provided to the user via an output component such as a speaker, headphones, or any other suitable output device.

It will be appreciated that method 100 can adapted or implemented to help reduce suffering from post-traumatic stress disorder (PTSD), Anxiety, Obesity, ADHD, Schizophrenia, and/or other psychological conditions.

According to a variation, the state-songs of the present disclosure can facilitate predictive analytics and personalized medicine. For instance, a user's state song can be singularly unique to that individual. From a clinical perspective this helps move health sciences past group statistics toward modelling, monitoring and intervention of a highly individualized and predictive nature. Furthermore, the parallel imbedded nature of biometrics is rich soil for deep learning. Aimed towards bio-simulations with individual accuracy, methods of the present disclosure can define the way intelligent agents learn, diagnose, predict, prevent and intervene. In addition, integration of state songs and holography may provide a platform on which to evolve and utilize a truly intelligent AI.

It will be appreciated that any of the methods described herein may be implemented in an application. The application may be software embodied on a computer readable medium which when executed by a module of a computer system performs a sequence of steps. The application may be a mobile application or application software configured to run on smartphones, tablets computers, and/or other mobile devices. The application may be a web-based programming language and/or web-based computing platform. The application may be a computer programming language that is concurrent, class-based, object-oriented, and design to have minimal implementation dependencies (e.g., Java programming language).

FIG. 5 schematically depicts a system 100 for controlling state dependent behavior of a user. The system 100 may include a computer device that can display information to a user and receive user input, respectively. The computer device can include a mobile device. A mobile device is defined as a processing device routinely carried by a user. It typically has a display screen with touch input and/or a keyboard, and its own power source. The system 100 may include biometric data capture devices (e.g., sensors), storage devices, and/or transmission devices.

The system 100 can be in communication with an application and/or a cloud computing platform. The application and/or cloud platform can be configured to perform any of the acts described herein. For instance, the cloud platform can be arranged to convert data (e.g., biometric data) to lines of sound, sounds and/or songs. In other embodiments, the cloud platform can be arranged to store and/or transmit data, sounds, and/or songs.

In other embodiments, the cloud platform and/or application can be arranged to manage intelligent agents and/or artificial intelligence. For instance, the cloud platform and/or application can include predictive simulation and/or health diagnostic agents. In an embodiment, the application and/or cloud platform can be arranged to perform sonificiation and/or include holographic intelligence systems.

The system 100 may include different modules 102-118 arranged to perform different functions. For instance, the system 100 may include one or more modules for biometrics data sonification, biometrics and state analysis, sound generations, state-song composition, state-song storage and access, user services and tools, biological systems modelling, and/or intelligent agents. According to a variation, the system 100 can include an ingest module 102 arranged to receive and/or store data including biometric data. The biometric data may include any suitable type of data, including, but not limited to, somatic data, EEG data, endocrine data, and/or user defined data. The system 100 can also include an encode module 104 arranged to encode or sonify data from the ingest module. The system 100 can include an MM/SM module 114 including playback devices, analytics and info, editing tools, data and info security, simulation models, and/or intelligent agents. In other embodiments, the system 100 may include input/output modules including dashboards and/or graphical user interfaces.

Figure 6:
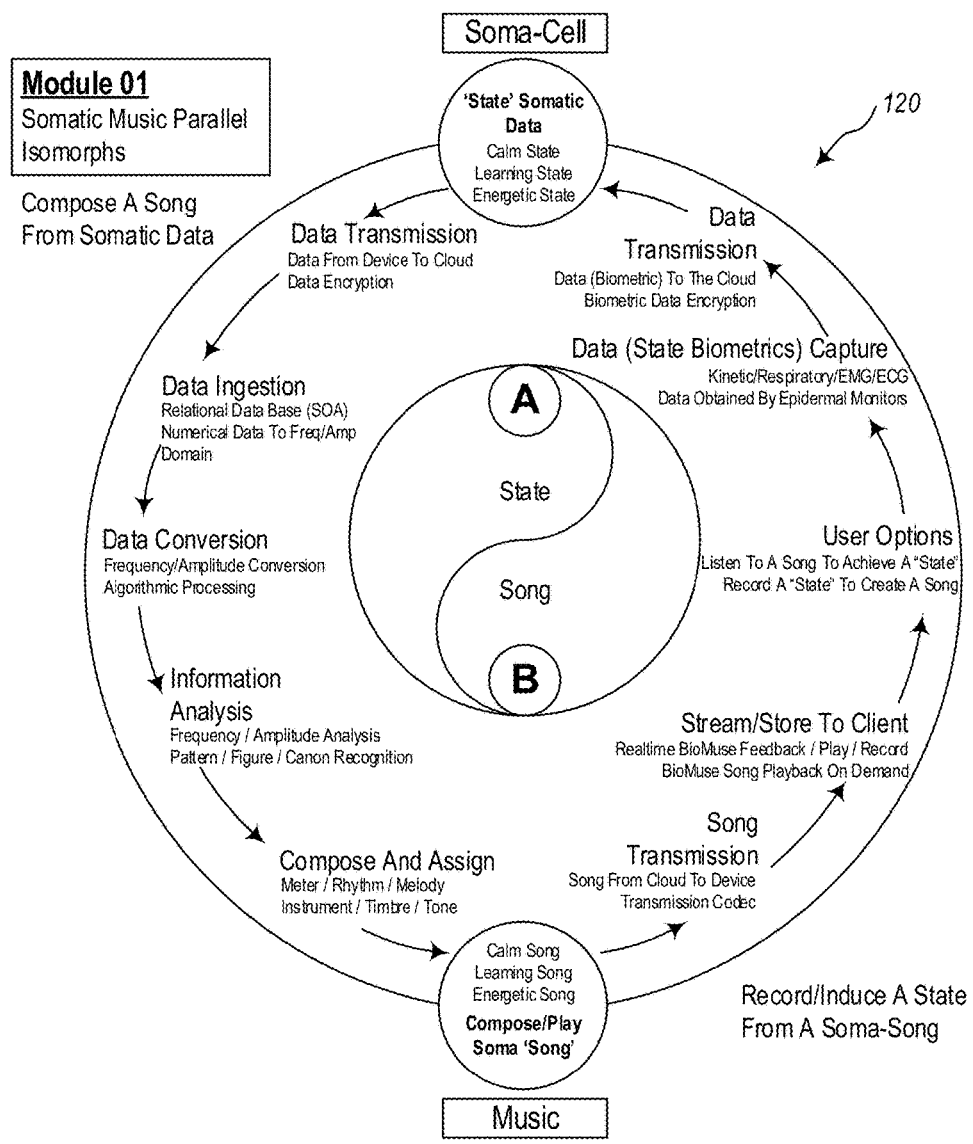
FIG. 6 illustrates a somatic module according to an embodiment.
Figure 7:
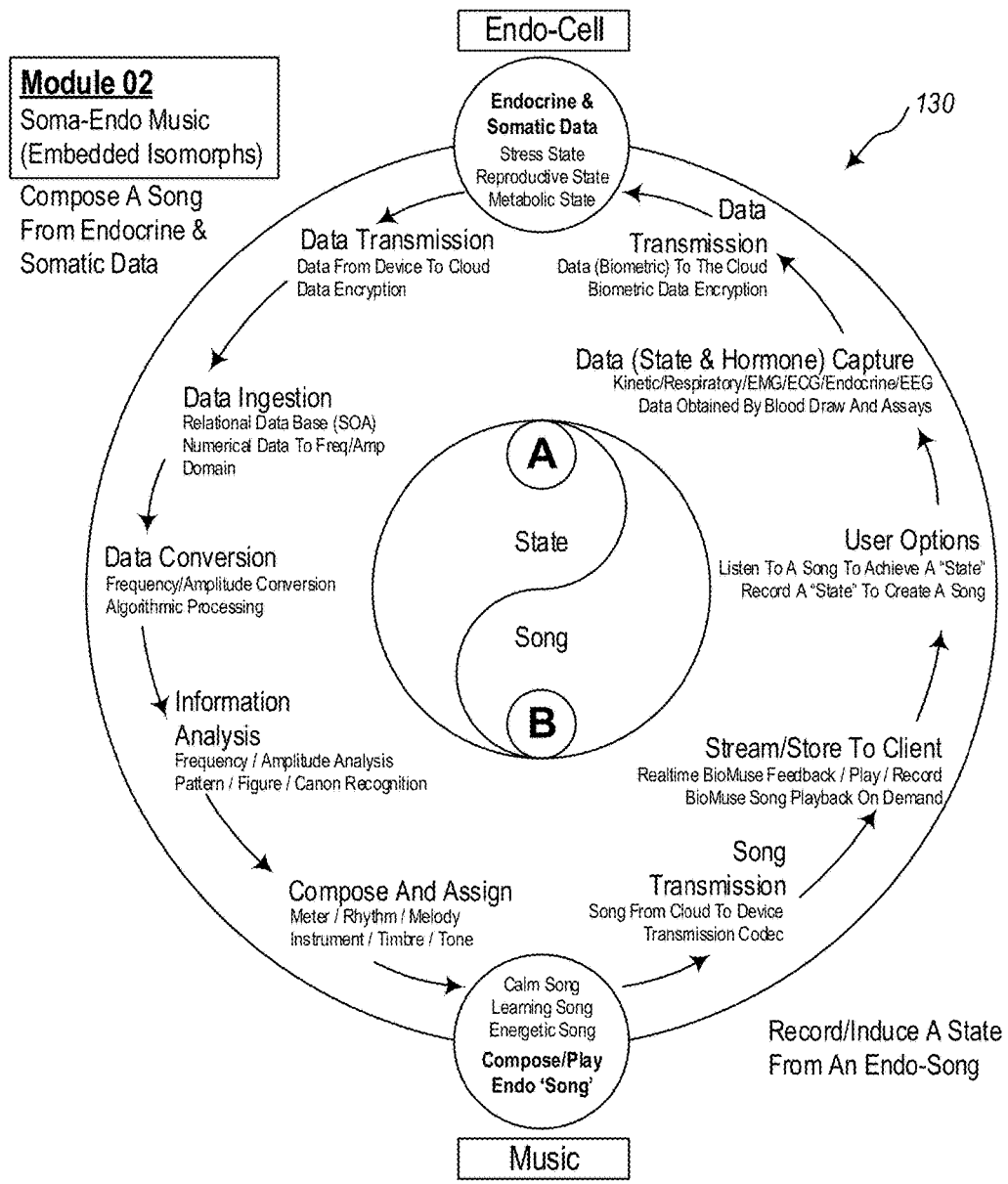
FIG. 7 illustrates an endocrine module according to another embodiment.
Figure 8:
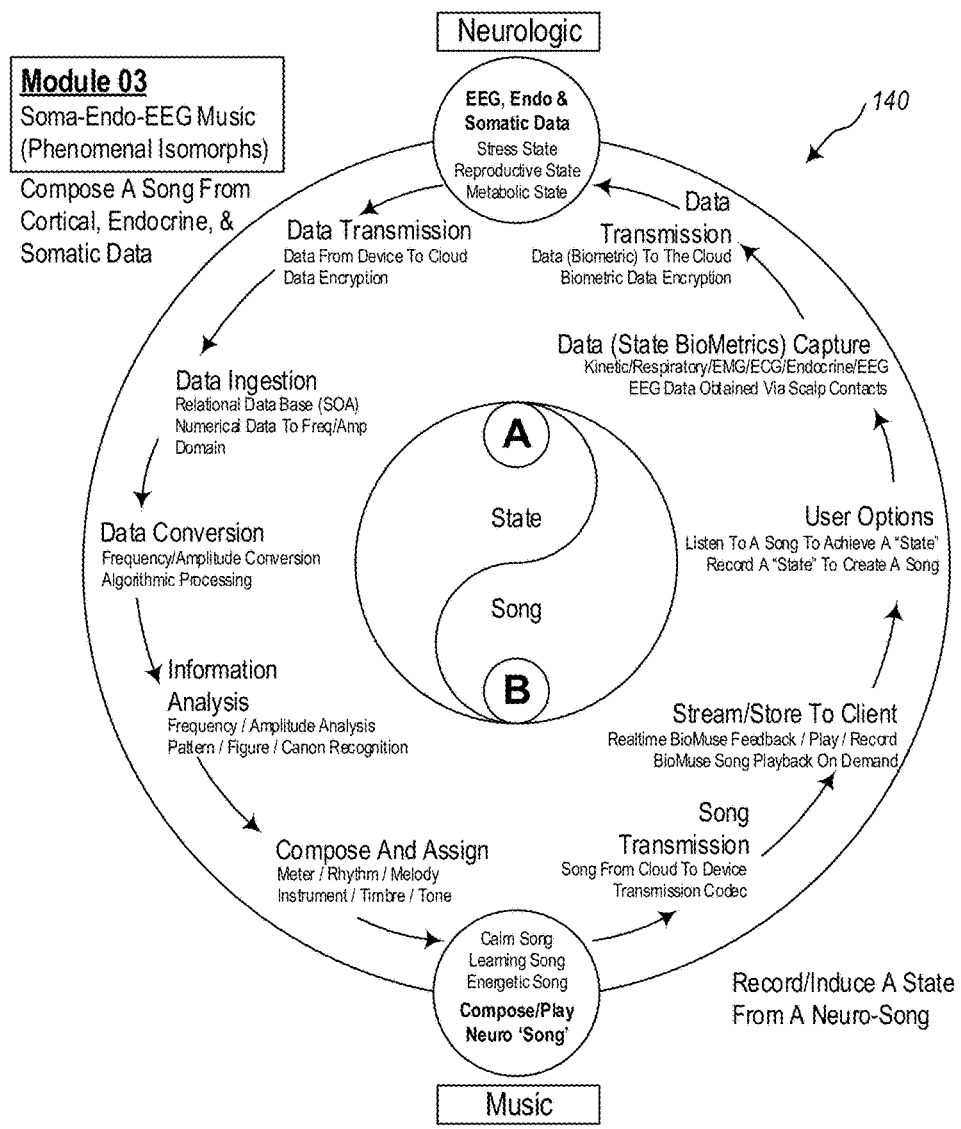
FIG. 8 illustrates an EEG module according to another embodiment.
Figure 9:
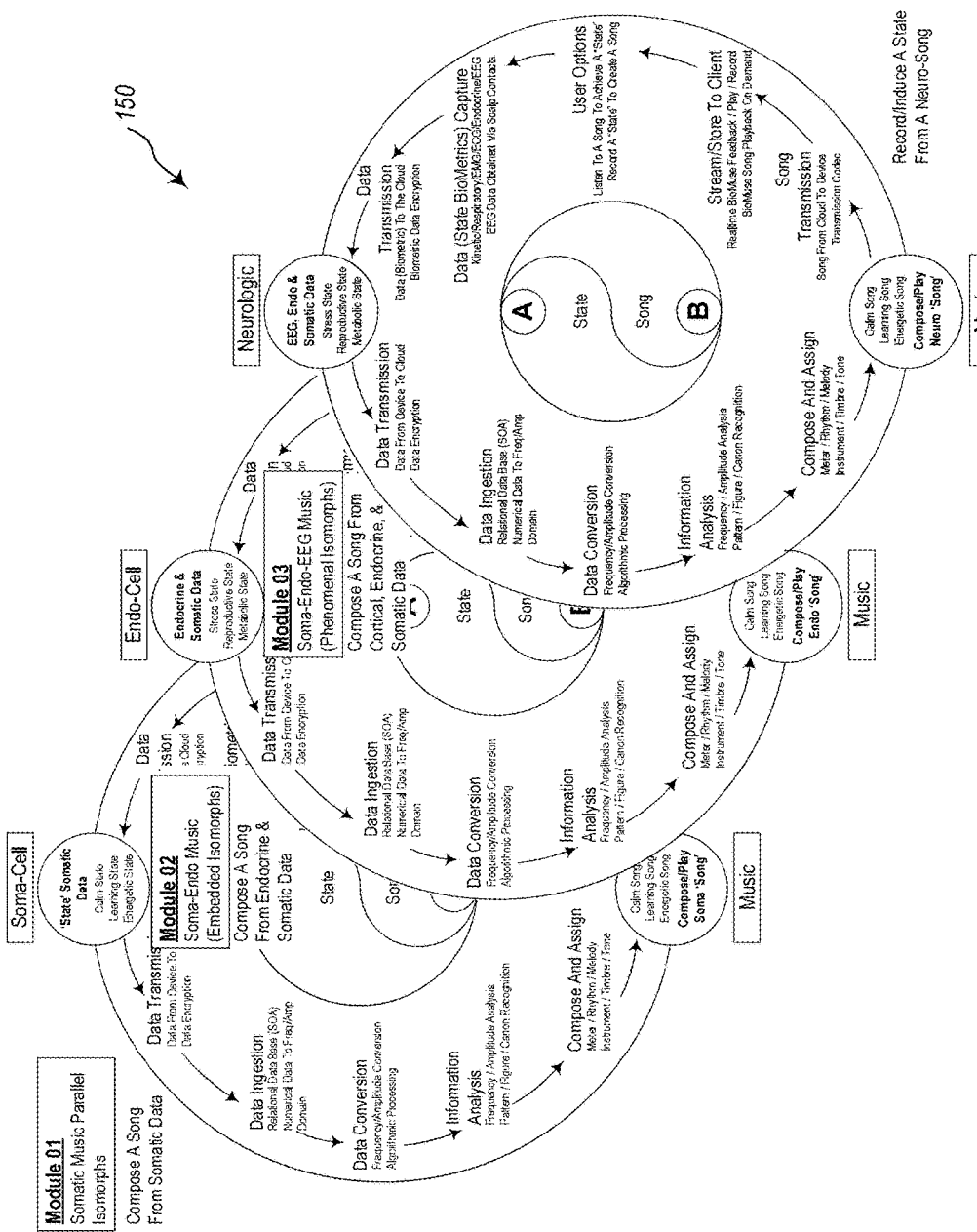
FIG. 9 illustrates a system of module integration according to an embodiment.
Figure 10:
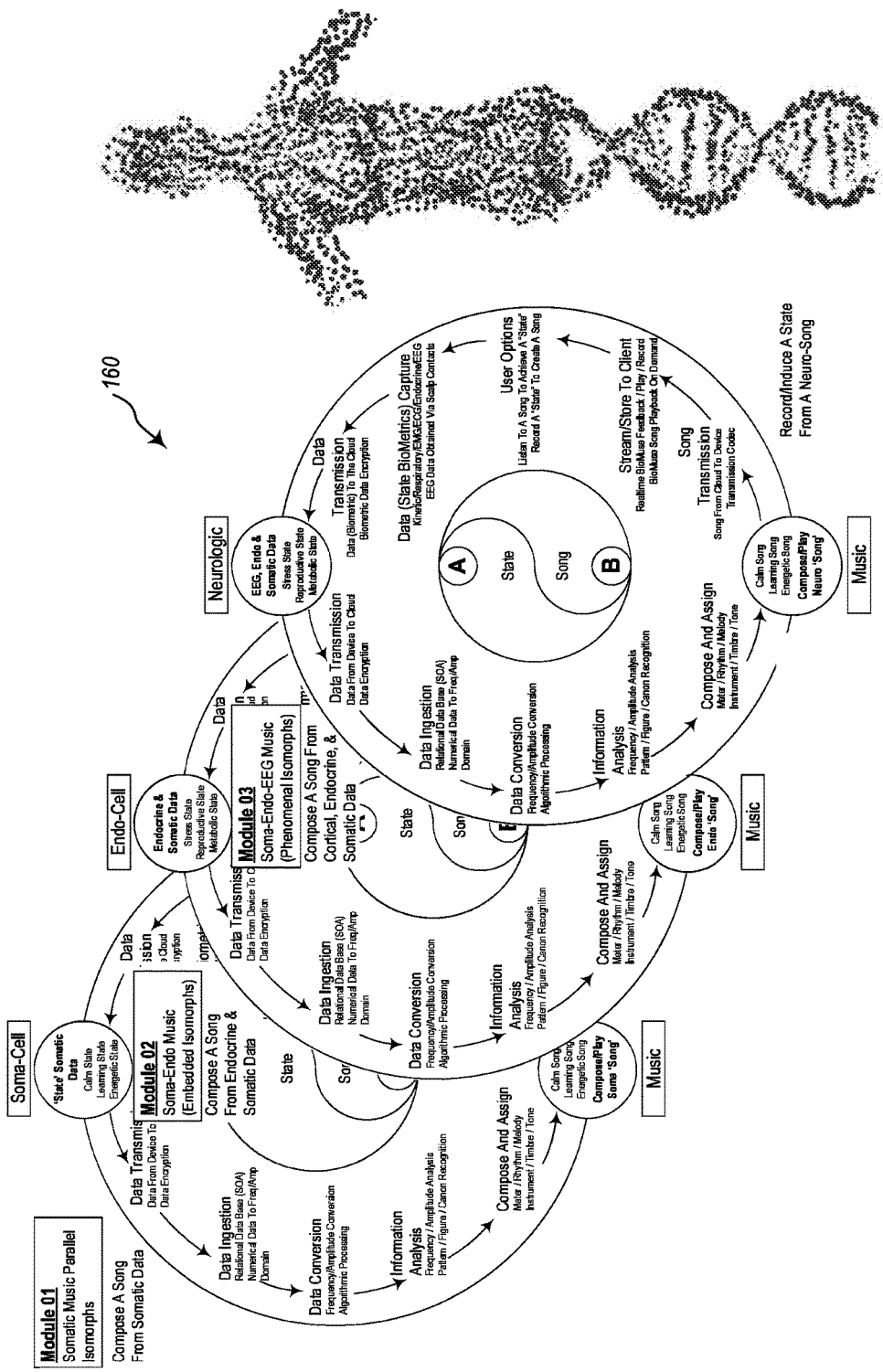
FIG. 10 illustrates a modelling system according to an embodiment.
Figure 11:
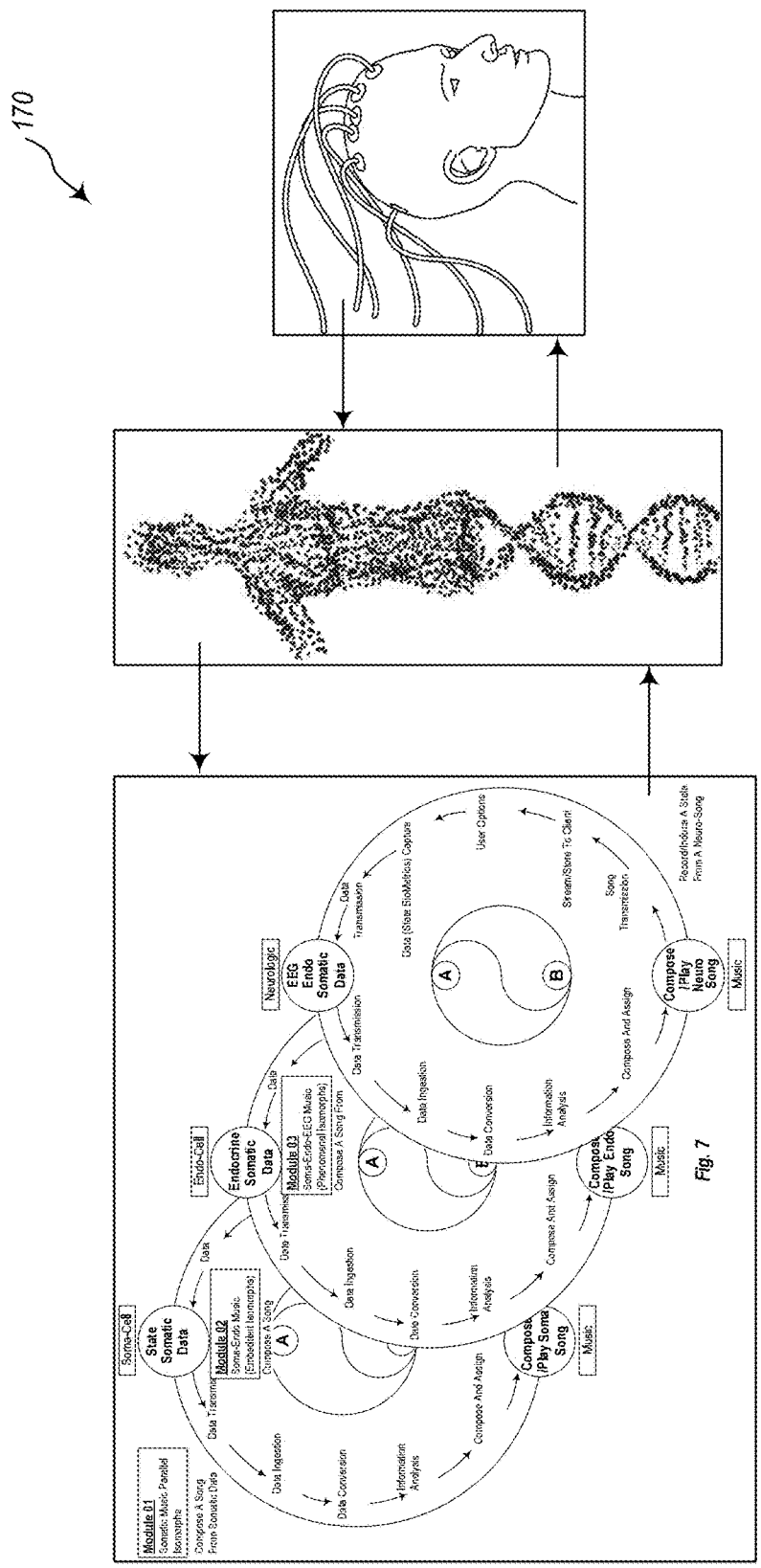
FIG. 11 illustrates a modelling system according to another embodiment.

FIG. 6 illustrates a somatic module 120 according to an embodiment. FIG. 7 illustrates a somatic module 130 according to an embodiment. FIG. 8 illustrates an EEG module 140 according to an embodiment. FIG. 9 illustrates a method 150 of module integration. FIG. 10 illustrates a method 160 of biometrics and sonimodi-modelling. The method 160 includes stacking modules with data integration and comparisons towards individualized medical models. FIG. 11 illustrates a method 170 of state song, simulation modeling and AI. The method 170 includes stacking modules with data integration and medical modelling toward biological intelligence.

Figure 14:
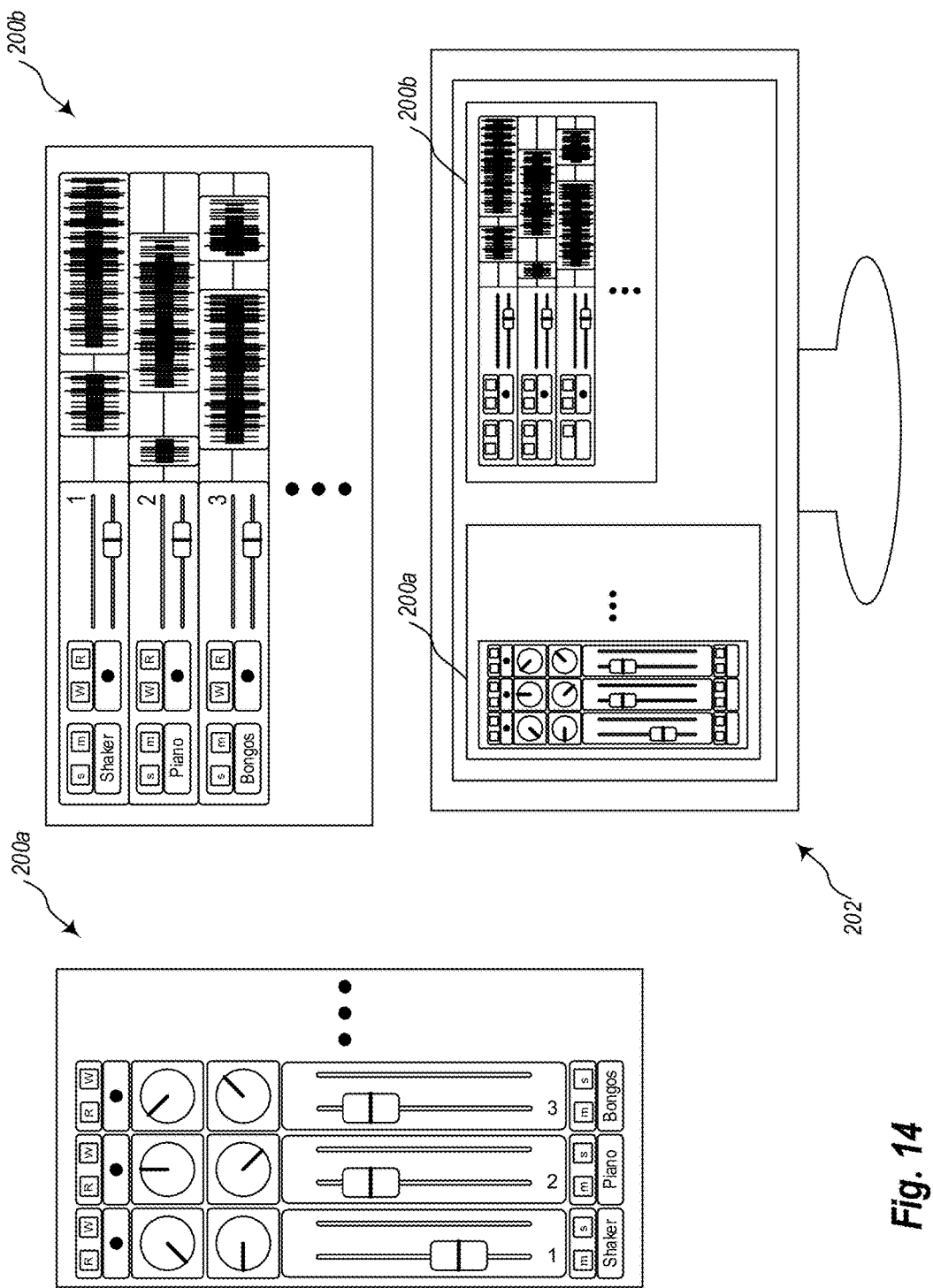
FIG. 14 illustrates a user interface according to another embodiment.

It will be appreciated that the system 100 can include one or more user interface through which the user is able to input or receive information. For instance, FIG. 12 illustrates a user interface 180 implemented on a mobile device 182. As seen, the user interface module 180 can be simplified to improve ease of use. FIG. 13 illustrates a user interface 190 implemented on a mobile device 192. The user interface 192 can include more options and controls for a more involved user. FIG. 14 illustrates two different user interfaces 200a and 200b implemented on a desktop computer 202. The user interfaces 200a and 200b can have a more a complex architecture adapted for analytics and modeling.

Figure 15:
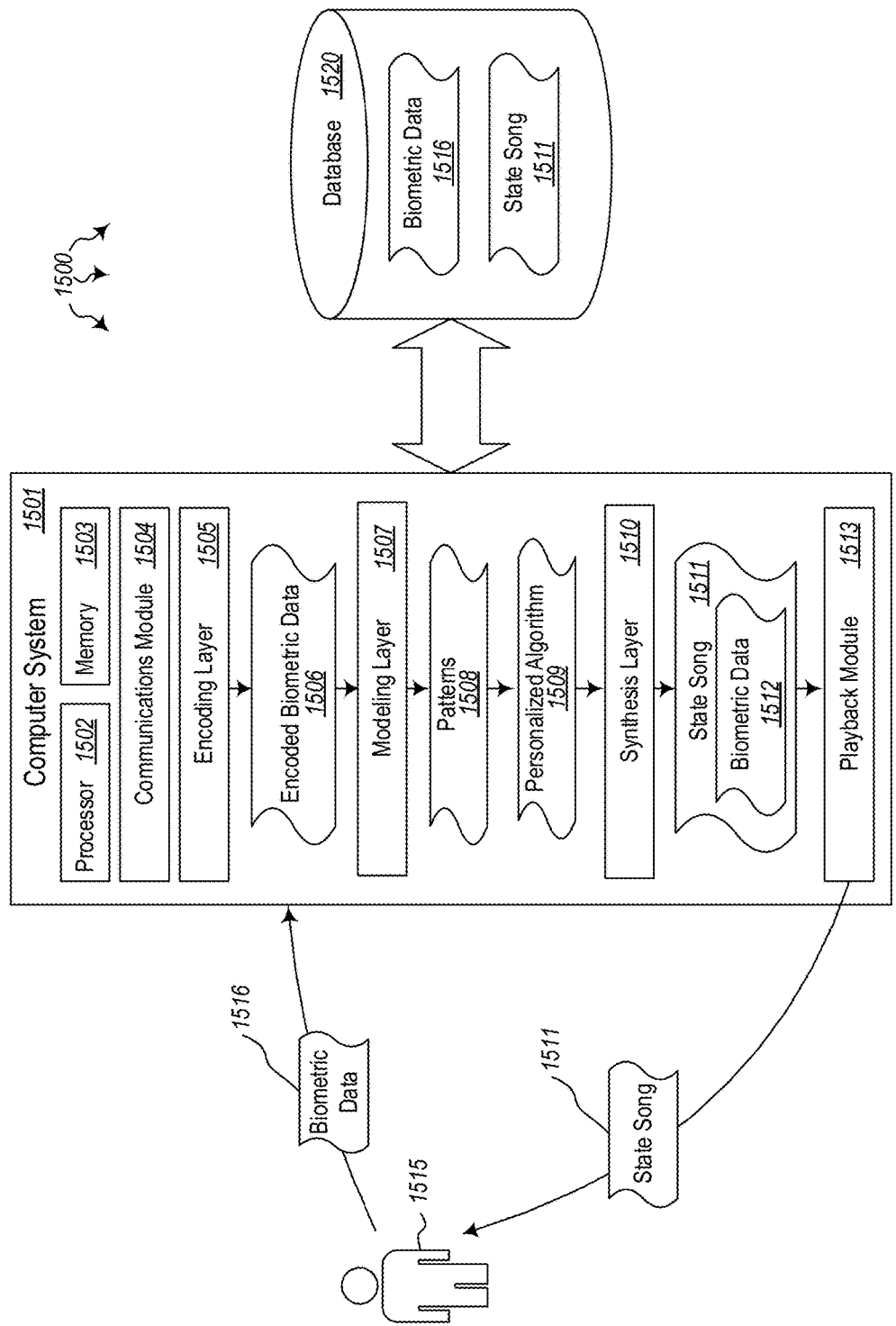
FIG. 15 illustrates a computing architecture in which embodiments described herein may operate.

FIG. 15 illustrates a computer architecture 1500 in which at least one embodiment described herein may be employed. The computer architecture 1500 includes a computer system 1501. The computer system 1501 includes at least one processor 1502 and at least some system memory 1503. The computer system 1501 may be any type of local or distributed computer system, including a cloud computer system. The computer system 1501 includes modules or layers for performing a variety of different functions. For instance, communications module 1504 may be configured to communicate with other computer systems. The communications module 1504 may include any wired or wireless communication means that can receive and/or transmit data to or from other computer systems. The communications module 1504 may be configured to interact with databases, mobile computing devices (such as mobile phones or tablets), embedded or other types of computer systems.

Computer system 1501 further includes an encoding layer 1505. The encoding layer may be configured to receive biometric data 1516 from a user (e.g. 1515) or from a computing device connected to the user. For example, the biometric data 1516 may be any type of data relating to a user's body including somatic data such as heart data (heart rate), lungs data (respiration rate), skin data (stress levels), vascular system (blood pressure), kinetic information (body position), endocrine system data, electroencephalogram (EEG) data, personal information (calendar, activities, relations, concerns, etc.) and other types of data. As shown in FIG. 17, each of these different types of biometric data may be captured and provided to an encoding layer or transcoding engine.

The encoding layer 1505 of computer system 1501 analyzes the received biometric data 1516 and encodes the data into data structures that can be modeled in the modeling layer 1507 using an algorithm that is specific to the user. Indeed, when the modeling layer 1507 models the encoded biometric data 1506, it identifies patterns 1508 that are unique to the user 15151. These patterns may be found in rhythmic recurrences of frequencies, tones, repeated highs and lows in certain measurements, or other patterns. These patterns match a user uniquely, and thus the use of these patterns to create a state song will result in a state song that is specific and unique to the user. The patterns 1508 are used to generate an algorithm that is fed to the synthesis layer 1510. The algorithm may represent one type of biometric data, or may represent many different types of biometric data.

The synthesis layer 1510 uses this personalized algorithm 1509, along with the encoded biometric data 1506 and generates a state song 1511 specific to a given biometric state 1512. For example, if the user 1515 is currently in a relaxed state, as evidenced by one or more forms of biometric data (e.g. low heart rate, low blood pressure, low stress, etc.), then the state song generated will correspond to the relaxed state. Many other states may be captured based on the biometric data. The synthesis layer may use the personalized algorithm along with one or more portions of music data or music knowledge to generate a song or soundscape that is pleasing to the ear. The playback module 1513 plays back the generated state song 1511 to the user 1515 to bring that user to the specified biometric state. For instance, if the user is agitated, the state song corresponding to a relaxed state may be played back to the user to bring the user to the relaxed state. The user's biometric data 1516 may be stored in a local or remote database 1520, along with any state songs 1511 that are generated. These concepts will be explained further below with regard to method 1600 of FIG. 16, along with the computing architectures shown in FIGS. 17A and 17B.

Figure 16:
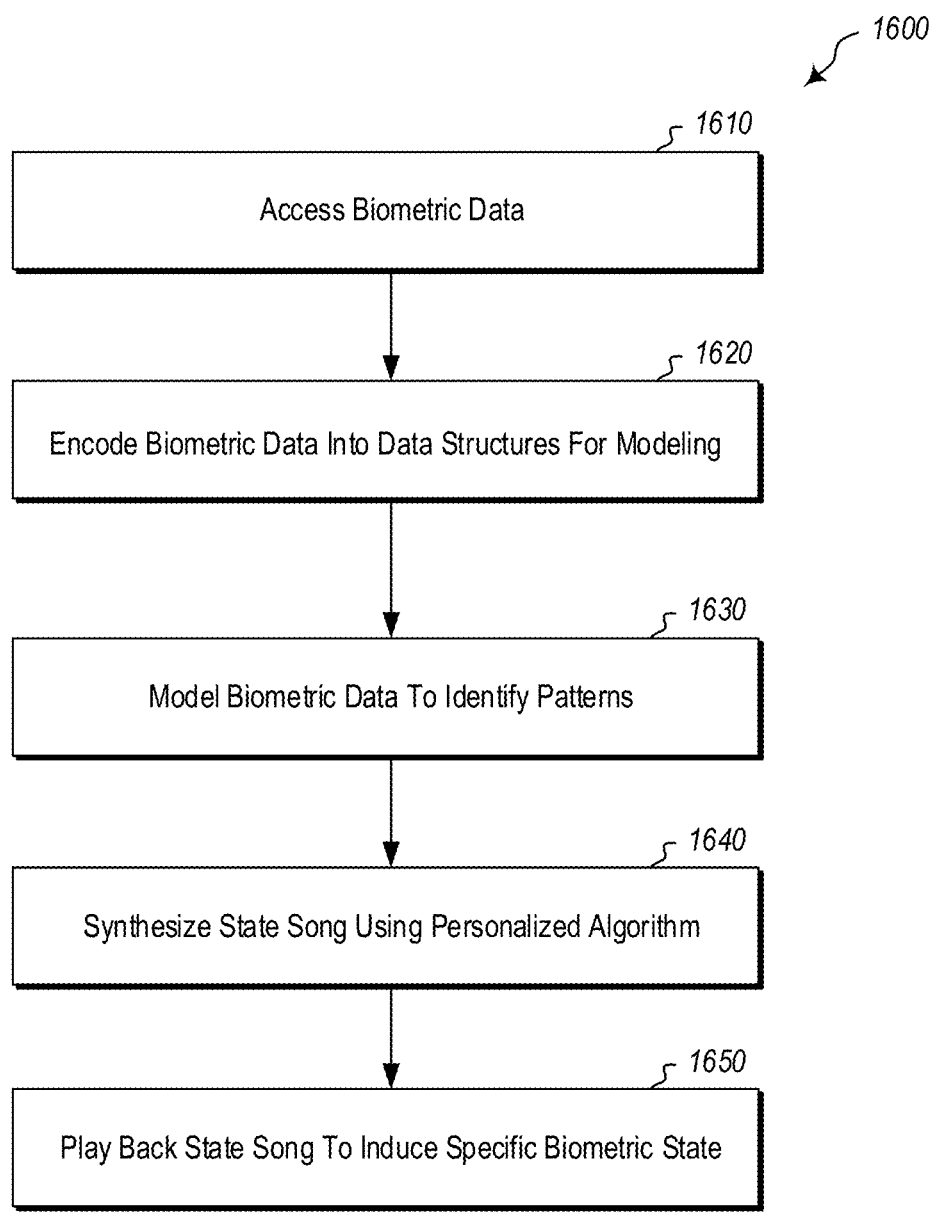
FIG. 16 illustrates a flowchart of a method for generating and playing back a personalized state song representing a target state of a user.

In view of the systems and architectures described above, methodologies that may be implemented in accordance with the disclosed subject matter will be better appreciated with reference to the flow charts of FIG. 16. For purposes of simplicity of explanation, the methodologies are shown and described as a series of blocks. However, it should be understood and appreciated that the claimed subject matter is not limited by the order of the blocks, as some blocks may occur in different orders and/or concurrently with other blocks from what is depicted and described herein. Moreover, not all illustrated blocks may be required to implement the methodologies described hereinafter FIG. 16 illustrates a flowchart of a method 1600 for generating and playing back a personalized state song representing a target state of a user. The method 1600 will now be described with frequent reference to the components and data of environment 1700 of FIGS. 17A and 17B.

Method 1600 includes accessing one or more portions of biometric data corresponding to one or more bodily systems of a user (1610). For example, the communications module 1504 may receive biometric data 1516 from various electronic devices including bodily system monitors, smart watches, EEG machines or other devices that produce biometric data. The data may be received via wired or wireless data connections. Alternatively, the encoding layer 1505 may directly access the biometric data 1516, for example, in cases where the data is stored on the database 1520.

The encoding layer encodes the biometric data 1516 into data structures that are configured for modeling using an algorithm 1509 that is specific to the user (1620). The modeling layer 1507 models the encoded biometric data to identify specified patterns 1508 in the encoded biometric data. The identified patterns are used to generate a personalized algorithm 1509 that corresponds with the identified patterns unique to the user (1630). Method 1600 further includes synthesizing a state song 1511 using the personalized algorithm, where the state song represents a specific biometric state for at least one bodily system (1640), and playing back the state song to the user to induce the user to the specific biometric state (1650).

Figure 17A:
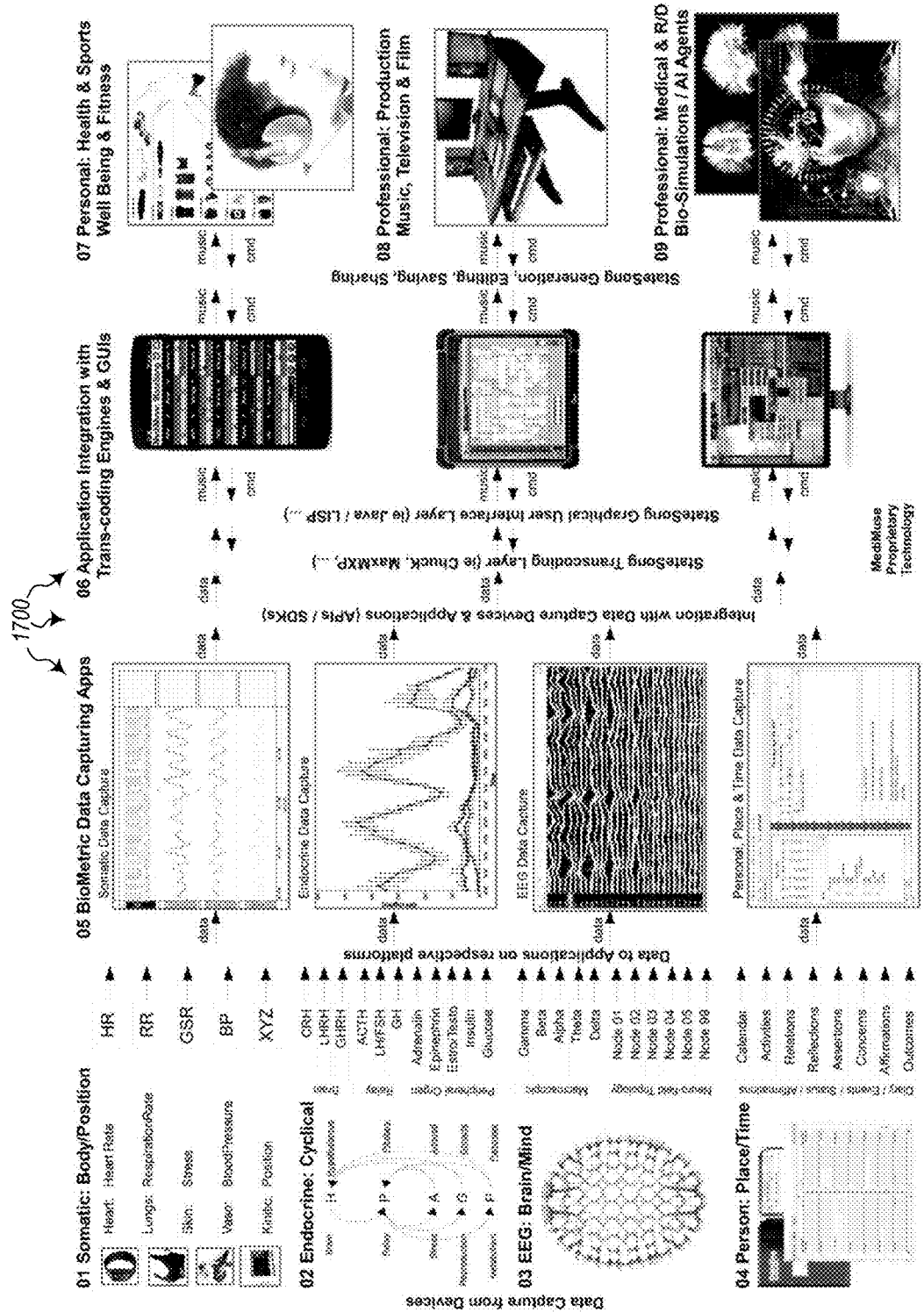
FIGS. 17A and 17B illustrate a system for generating and playing back a personalized state song representing a target state of a user.

As shown in FIG. 17A, Sections 01-05 depict example data types and devices that the system (1700 generally) can capture for encoding. It should be noted that the modules of the system shown are not limited to those depicted herein, and it will be understood that the embodiments described herein may be used to encode data from any biometric source into a state song. Moreover, the biometric data may be leveraged for parallel or other modeling and intelligence implementations (please see discussion of FIG. 5 above).

System 1700 thus converts biometric data from any device or application into music. This includes, but is not limited to heart rate, blood pressure, galvanized skin response, respiration rate, body temperature, body velocity, position, etc. The application layer, as depicted in Section 06, is configured to interface with any application via software development kits (SDKs), APIs, etc.

Section 02 depicts data in the endocrine system, which may be cyclical. System 1700 can convert endocrine data from any device or application into music. This includes existing, methods that capture and record hormone and other biological compound levels that can be measured from blood, lymph or spinal fluid.

Section 03 depicts EEGs that show brain activity. The system 1700 converts electroencephalograph data from any device or application into music. This includes methods and devices that capture and record brain Alpha, Beta, Delta, Gamma and Theta waves, as well as methods and devices that capture and record neuronal interference or spectral data from the cortex, cerebellum or mid-brain structures via external skull caps, electrodes, neural fabrics, or other brain-computer interfaces.

Section 04 depicts person, place and time data including calendar and locations data from any device or application into music. This include methods and devices that capture and record calendar elements, activities, relationships, reflections, assertions, concerns, affirmations and outcomes, or other information that can be represented quantitatively regarding a person's location, a person's plans, concerns or other activities that could affect the person's biometric state.

Section 05 depicts biometric data capturing applications which gather data and render graphs. The biometric data capturing applications can be integrated with SDKs that allow data to be captured by the system's application layer via API, REST, SOAP, XML, JSON, WSDL or other protocols. Many types of biometric data capturing applications exist in fields such as science, technology, engineering, medical, and health and wellness. Independent of data capturing method, the system 1700 will integrate the received biometric data for encoding, and can create a virtual twin model of the person using that data. This will be explained further below.

Sections 06-09 describe system 1700's conversion and GUI layers, as well as the spectrum of uses across sectors such as health and wellness, fitness, music, medicine and research & development, and the various platforms upon which the system can operate to achieve objectives that have root in state-dependent behavior modification. The embodiments herein aim to change the user's biometric state using music that is specifically tailored to the user, and may further be used to potentially alter the user's behaviors. This level of use is primarily conducted between the user, a biometric device and computer 1501 (i.e., phone, laptop, tablet, etc.). Access to cloud services and applications, compliant with data protections standards (i.e., HIPPA, PCI, etc.) are discussed in Sections 10-12 below.

Section 06 includes trans-coding engines & GUIs. The transcoding engines capture and encode biometric data using algorithmic conversions of the data that are personalized to the user. The transcoding engines then ascribed sound attributes programmed within the conversion layer. This layer can be coded in numerous languages including, but not limited to, ChucK, MaxMXP, PureData and SuperCollider.

Sound attributes include, but are not limited to, instrument selections (piano, strings, shakers, etc.), natural sounds (frogs, drops, wind, etc.), user generated sounds (recorded, programmed), sampling rates, 7.1 sound locations, effects (reverb, chorus, compression, phase, etc.) and other sound items. A graphical user interface is provided that grants the user access to sound options provided from the transcoding engine, and allows the sound attributes applied to each line of data to be controlled. The GUI layer can be programmed from a multiple languages including, by example, but not limited to, Java, LISP and HTML5. The GUI lets users take any line of data and multiply it, applying different attributes to each copy. This allows even a single biometric device to drive multiple lines of sound.

The three devices in Section 06 surrounding the encoding engine and GUI characterize examples of the GUI's of varying designs running on a spectrum of computer systems for broad range of purposes, including but not limited to, 1) health and wellness applications such as sports training, track & field, cycling, archery, etc, 2) state and behavior including relaxation, meditation, attention, learning, addiction, 3) music production and distribution, including an application to create 'Personalized' biometric based music for distribution, and a module for professional tools for music, television and film production, as wells as a platform for medical music including advanced modeling and intelligent agents.

These devices and GUI further provide 4) personalized modeling and virtual twinning for somatic data (heart rate, respiration rate, blood pressure, GSR), endocrine data (metabolic, reproductive, stress, immunological data, etc.), neurological, immunological, or data from other systems. The devices can also provide 5) personalized medicine with intelligent personal and model monitoring, and intelligent diagnostic and interventive agents.

Section 07 of FIG. 17A depicts a personal health, wellness and fitness category which exemplifies uses for state song technology in health, wellness and fitness. Some of these uses may include personal fitness, sports improvement, meditation, hypnosis, alleviating anxiety and trauma based disorders, improving learning disorders and disabilities, improving attention disorders and disabilities, generating personalized music, shared and group music for counseling, meditation, concert and dancing music, etc. Biometric devices that can be used to capture data for generation of state songs includes head and neck devices, chest, back and torso devices, arm devices, wrist devices, hands devices, midsection devices, legs devices, knees devices, feet/shoe devices, headset devices, earbud devices, hands-free devices, medical equipment that captures biometric data, etc.

Section 08 depicts a professional category including generation of state songs that could be used in production for music, television & film. State songs may be used in personal & professional music production on mobile phones, tablets, laptops, desktop computers and other computational devices. A state song production module is designed to integrate with professional audio and video tools. Section 09 is similar, and is designed to show professional medical and research and development uses, biosimulations and AI agents. The system 1700 may provide access to artificial intelligence tools that enhance the state songs and make the songs more appealing to human users. The system also provides personalized simulation modeling and virtual twins. Localized agents can work offline from the cloud, but can, ultimately, connect to deeper (data protected) functionalities, services, updates, etc through the cloud.

Figure 17B:
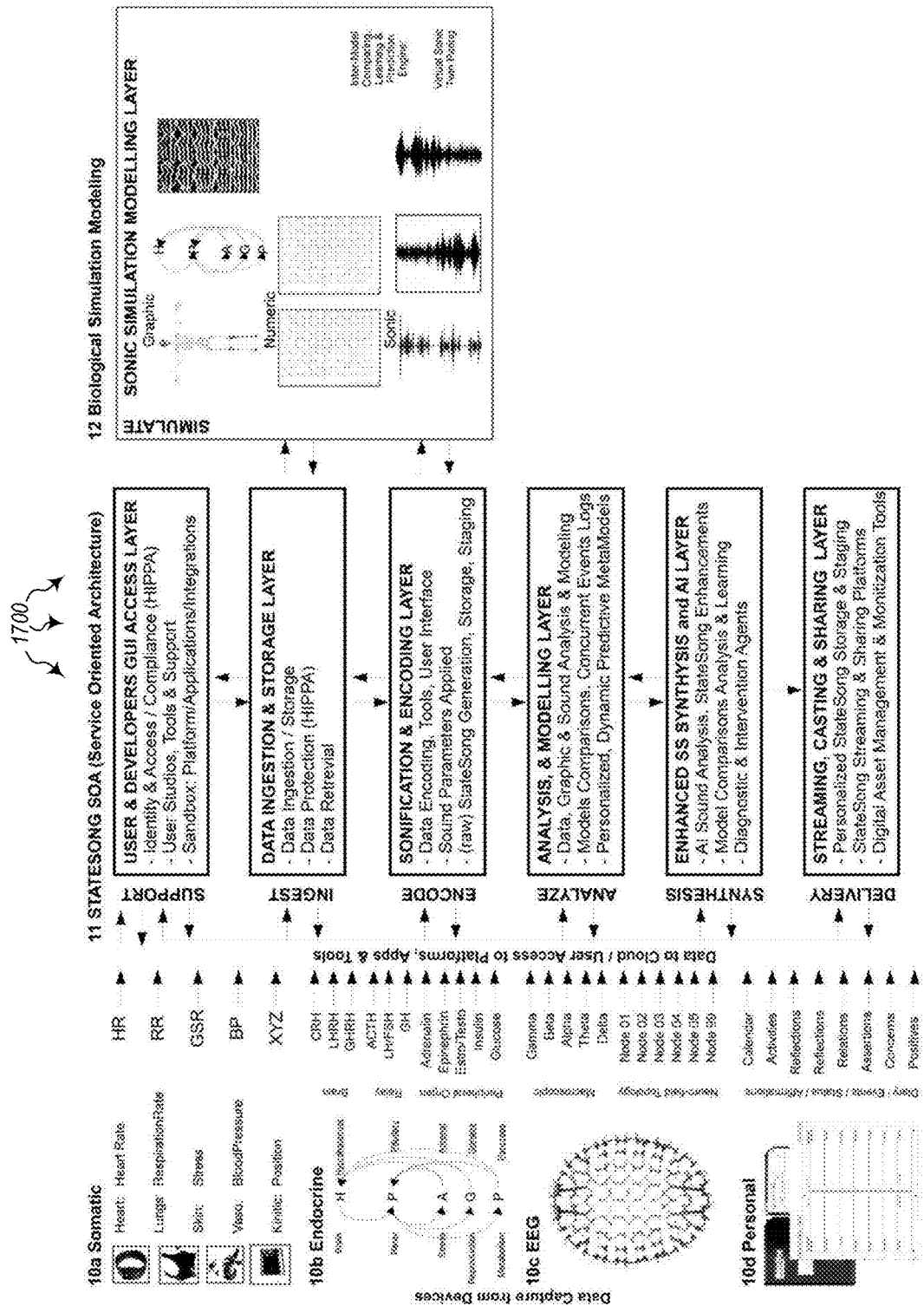

Section 10 of FIG. 17B describes a scenario in which biometric and state song data are stored to the cloud (e.g. database 1520 of FIG. 15). The system 1700 transmits personal and biometric data from any device, application or platform to the state song cloud for storage and staging for advance options and functions provided by a service oriented architecture (SOA). Data transport and storage is designed to be compliant with relevant standards such as HIPPA and other health-related data protection acts. Data is stored, protected and staged for access by authorized users. The data may be used by advanced encoding and sound tools and applications, advanced modeling tools and applications, and advanced intelligence tools and applications.

Section 11 depicts a service oriented architecture which is a configuration of componentized tools, functions and services accessible via the cloud. The services may include: support tools, user and developer tools, access, identity, security and compliance layers, user virtual studios, sound libraries and music production tool, development tools, SDKs, platform and application sandboxes, data ingestion, protection and retrieval, data ingestion and storage, data protection, encryption and standards compliance, and other types of data access.

The SOA of section 11 in FIG. 17B provides encoding tools and applications including user and developer data encoding tools and applications, user and developer sound tools and applications, user and developer state song tools and applications, analysis and modeling tools and applications, data, graphic & sound analysis tools, personal models, model comparisons, concurrent event logs, personal algorithmic dynamic predictive simulations on a digital virtual twin that has and is based on the user's same biometric data. Synthesis intelligence tools and applications including sound analysis and state song enhancements are also provided by the SOA.

The SOA of Section 11 also provides Data2Mind models, prototypes, applications, platform, holo-infomatic intelligence: diagnostic and interventive agents, sharing, archiving, monetization, personalized state song storage and sharing, state song streaming & sharing platforms, digital asset management & monetization tools.

Section 12 depicts sonic simulation (isomorphic) modeling. This sonic simulation depicts multiple representations of an individual's physiology data including graphical, numerical, and sonic representations. The representations illustrate how data is monitored, tracked, gathered and graphically depicted. Moreover, the representations, as isomorphs, aided by artificial and 'organic' intelligence, present embodiments where modality models can 'learn' from each other. Further, these representations can be leveraged, and 'pushed and pulled', to provide predictive graphical, numerical and sonic renderings of the models, and thus the individual's states that it purports to model.

The biometric and personal data types that can be individually and interactively modeled are not limited to the list below. Indeed, somatic, endocrinological, neurological, immunological, medications, personal data (activities, reflections, assertions, concerns, other data types) can be used to generate highly representative perpetual biopsychosocial models of an individual. Perpetually gathering biometric data from bodily subsystems, the system 1700 generates perpetual sonic representations, 'isomorphs' (algorithms) of each respective subsystem's activities. The 'integration' of subsystem algorithms represents a larger algorithmic isomorph' or 'meta algorithm' of the individual.

In "Personalized Medicine" parlance, the state song system is providing a new 'Pairing Technology', where the results are 'Virtual Sonic Twins' (VSTs). VSTs can generate state songs from perpetual data gathering systems, and use these state songs to monitor, then predict, and ideally regulate the sonic twin. Then, ultimately, the VST can be applied for utilization with its human twin for monitoring, diagnostics, predictive analysis, interventive agents, state control, behavior modification and other uses. In gestalt, the integration of the models is a perpetual running algorithm, a 'virtual twin' of an individual, upon which intelligent agents of the system 1700 can analyze, diagnose, predict and act upon the digital twin and subsequently, or in parallel, the human or robotic twin. The algorithms can control an android, or the functions of a prosthetic device, or a swarm of robot bees pollinating crops, for example.

In some embodiments, the system 1700 may be configured to identify relationships between different types of biometric data 1516 as part of modeling the encoded biometric data 1506. For instance, the system 1700 may determine that a relationship exists between heart rate and EEG gamma wave data, or between endocrine cycles and blood pressure, or activity data, or between any of the variety of different types of biometric data. When these relationships are identified, the modeling layer 1507 may use the relationships when generating the personalized algorithm. Thus, the modeling layer 1507 may implement as input the identified relationships between the different types of biometric data and the encoded biometric data 1506. Using these relationships and data, the user-specific, personalized algorithm 1509 may be generated.

The encoding performed on the biometric data may be performed at a transcoding engine that includes an encoding layer configured to convert the biometric data into musical elements by mapping the biometric data according to sampling rate, filters, reverb or compression (see Section 06 of FIG. 17A). The musical elements can be notes (i.e. tones of a specific frequency), sounds of a musical instrument (such as a drum or a trumpet), soundscapes (e.g. rainfall or birds chirping), or any other type of musical element. In some cases, a default mapping is established for each type of biometric data. For instance, a heartbeat may be mapped to a drum, kinetic movements may be mapped to a lead guitar, EEG theta waves may be mapped to the sound of waves crashing on a beach, etc. Virtually any type of mapping is possible from any type of biometric data to any type of sound element.

The mapping may be made according to user input specifying which type of biometric data is to be mapped to a specific instrument or soundscape. Additionally or alternatively, an artificial intelligence engine may be implemented to learn musical patterns that make music acoustically desirable. The artificial intelligence (AI) engine may analyze many thousands or millions of musical compositions or soundscapes that are determined to be acoustically desirable. The AI engine may identify common elements among the compositions, and use those elements or patterns when mapping the different types of biometric data to an instrument or soundscape. Thus, in this manner, the mapping from encoded biometric data 1506 to actual music may be performed by an AI engine, or may be performed according to another program or user input.

Once the state song 1511 is generated, it is played back to the user 1515. This playback may be in reaction to the user reaching a specified, undesirable biometric state 1512. For example, a returned soldier may have slipped into an undesirable post-traumatic stress disorder (PTSD) state. A state song generated from that user's earlier relaxed state may be played back to the user to induce him or her to a relaxed state. Alternatively, the state song 1511 may be played back to the user 1515 proactively to prevent the user from reaching a specified, undesirable biometric state. As such, the state song may be used to amp the user up for an event such as a sport or competition, or may be used to help the user relax and fall asleep. Professionals may use a state song to induce a period of high brain activity, or to get "in the zone," or to clear their mind of trivial matters. As such, state songs may be used by professionals including doctors, lawyers, accountants, engineers, government officials, film actors, athletes, or other types of workers.

At least in some embodiments, this state change in a user's body from disheveled to concentrating, or from angry to relaxed, or from lethargic to energetic may be measured and documented. Various devices including heart rate monitors, blood pressure monitors, endocrine cycle monitors, EEGs or other biometric data gathering devices may be used to measure the changes in the user that occur as a result of playing back the state song 1511. Some state songs may be more effective than others for achieving a specified state change. As such, these state songs may be prioritized over others. A user's state songs may also be refined over time to be more effective at causing the desired change in state.

The biometric data gathering process may also be refined over time. Indeed, as data comes in from various body system monitors, that data may be filtered for noise. The system 1700 may include a filtering layer that is configured to filter at least some of the identified noise in the biometric data. Thus, when the system is identifying patterns in the encoded biometric data 1506, the noise can be identified and filtered out, leaving only the useful biometric data. Once the noise has been filtered out, the artificial intelligence layer will have an easier time mapping and providing musical elements as input to the synthesis layer 1510 indicating how the state song 1511 is to be generated. Genre filters may also be applied for the biometric data 1516. For instance, a classical music filter may be used based on the type of biometric data that is received, or a rock music filter may be used. This genre filter indicates generally what type of musical elements the AI engine should look for when providing musical elements to the synthesis layer to generate the state song.

Once created, the state song may be shared with other users. The system 1700 includes a sharing layer that provides the generated state song to other users. Many file sharing platforms may be used, including links to the files stored in the database 1520. In some cases, the state songs files are encrypted and are only accessible to authenticated users. Because the state songs are based on biometric data, which is typically protected as private information, the state songs may be stored in a legally compliant manner (e.g. HIPAA-compliant), whether they are stored locally or on the cloud. The user's biometric data and/or state songs may be moved to a service oriented architecture (e.g. Section 11 of FIG. 17B) that provides services including distributed processing and distributed storage.

The system 1700 may also provide a graphical user interface (GUI) that allows users to specify how biometric data from different biological systems is to be mapped to sounds, instruments, or soundscapes. The user may provide inputs indicating which types of biometric data should be mapped to which musical elements, or which musical genres should be used when mapping biometric data to musical elements. The GUI allows users to visualize the accessed biometric data 1516, the encoded biometric data 1506 and/or the generated state song 1511. Each state song may have a corresponding label that indicates its intended state 1512 (i.e. the state into which the user desires to transition). The GUI may also include a graph that is an isomorphic representation of the biometric data. The isometric model is a virtual or digital twin of the user, and may be used (and reused) to generate state songs for the user. The user may also use the GUI to indicate which endogenous music (i.e. biometric, personal music) is to be combined with which exogenous music to generate a given state song. The GUI thus allows for a variety of inputs that can control the generation of the state song.

Thus, using the systems described herein, biometric data may be gathered, encoded and mapped to musical elements to create a state song. The state song can induce the user to a given mental or physical state. The state song may be based on an endocrinological model which spurs insulin generation in pancreas or spurs estrogen production to increase fertility, it may be based on a somatic model which reduces heart rate, blood pressure or stress, it may be based on a brain model which increases cognitive ability or clears the mind of unnecessary clutter. As can be seen, the state song is unique to each user, and can be used to produce a variety of verifiable, measurable results in changing a user's state.

Many of the elements described in the disclosed embodiments may be implemented as modules. A module is defined here as an isolatable element that performs a defined function and has a defined interface to other elements. The modules described in this disclosure may be implemented in hardware, a combination of hardware and software, firmware, or a combination, all of which can be behaviorally equivalent. Modules may be implemented using computer hardware in combination with software routine(s) written in a computer language. It may be possible to implement modules using physical hardware that incorporates discrete or programmable analog and/or digital hardware. Examples of programmable hardware include computers, microcontrollers, microprocessors, application-specific integrated circuits, field programmable gate arrays, and complex programmable logic devices.

As noted above, the application may be software embodied on a computer readable medium which when executed by a processor component of a computer device performs a sequence of steps. The application may be a mobile application or application software configured to run on smartphones, tablets computers, smart watches, and/or other mobile devices. Moreover, embodiments of the present disclosure may comprise or utilize a special-purpose or general-purpose computer system that includes computer hardware, such as, for example, one or more processors and system memory, as discussed in greater detail below. Embodiments within the scope of the present disclosure also include physical and other computer-readable media for carrying or storing computer-executable instructions and/or data structures. Such computer-readable media can be any available media that can be accessed by a general-purpose or special-purpose computer system. Computer-readable media that store computer-executable instructions and/or data structures are computer storage media. Computer-readable media that carry computer-executable instructions and/or data structures are transmission media. Thus, by way of example, and not limitation, embodiments of the disclosure can comprise at least two distinctly different kinds of computer-readable media: computer storage media and transmission media.

Computer storage media are physical storage media that store computer-executable instructions and/or data structures. Physical storage media include computer hardware, such as RAM, ROM, EEPROM, solid state drives ("SSDs"), flash memory, phase-change memory ("PCM"), optical disk storage, magnetic disk storage or other magnetic storage devices, or any other hardware storage device(s) which can be used to store program code in the form of computer-executable instructions or data structures, which can be accessed and executed by a general-purpose or special-purpose computer system to implement the disclosed functionality of the disclosure.

Transmission media can include a network and/or data links which can be used to carry program code in the form of computer-executable instructions or data structures, and which can be accessed by a general-purpose or special-purpose computer system. A "network" is defined as one or more data links that enable the transport of electronic data between computer systems and/or modules and/or other electronic devices. When information is transferred or provided over a network or another communications connection (either hardwired, wireless, or a combination of hardwired or wireless) to a computer system, the computer system may view the connection as transmission media. Combinations of the above should also be included within the scope of computer-readable media.

Further, upon reaching various computer system components, program code in the form of computer-executable instructions or data structures can be transferred automatically from transmission media to computer storage media (or vice versa). For example, computer-executable instructions or data structures received over a network or data link can be buffered in RAM within a network interface module (e.g., a "NIC"), and then eventually transferred to computer system RANI and/or to less volatile computer storage media at a computer system. Thus, it should be understood that computer storage media can be included in computer system components that also (or even primarily) utilize transmission media.

Computer-executable instructions comprise, for example, instructions and data which, when executed at one or more processors, cause a general-purpose computer system, special-purpose computer system, or special-purpose processing device to perform a certain function or group of functions. Computer-executable instructions may be, for example, binaries, intermediate format instructions such as assembly language, or even source code.

Those skilled in the art will appreciate that the disclosure may be practiced in network computing environments with many types of computer system configurations, including, personal computers, desktop computers, laptop computers, message processors, hand-held devices, multi-processor systems, microprocessor-based or programmable consumer electronics, network PCs, minicomputers, mainframe computers, mobile telephones, PDAs, tablets, pagers, routers, switches, and the like. The disclosure may also be practiced in distributed system environments where local and remote computer systems, which are linked (either by hardwired data links, wireless data links, or by a combination of hardwired and wireless data links) through a network, both perform tasks. As such, in a distributed system environment, a computer system may include a plurality of constituent computer systems. In a distributed system environment, program modules may be located in both local and remote memory storage devices.

Those skilled in the art will also appreciate that the disclosure may be practiced in a cloud computing environment. Cloud computing environments may be distributed, although this is not required. When distributed, cloud computing environments may be distributed internationally within an organization and/or have components possessed across multiple organizations. In this description and the following claims, "cloud computing" is defined as a model for enabling on-demand network access to a shared pool of configurable computing resources (e.g., networks, servers, storage, applications, and services). The definition of "cloud computing" is not limited to any of the other numerous advantages that can be obtained from such a model when properly deployed.

A cloud computing model can be composed of various characteristics, such as on-demand self-service, broad network access, resource pooling, rapid elasticity, measured service, and so forth. A cloud computing model may also come in the form of various service models such as, for example, Software as a Service ("SaaS"), Platform as a Service ("PaaS"), and Infrastructure as a Service ("IaaS"). The cloud computing model may also be deployed using different deployment models such as private cloud, community cloud, public cloud, hybrid cloud, and so forth.

Some embodiments, such as a cloud computing environment, may comprise a system that includes one or more hosts that are each capable of running one or more virtual machines. During operation, virtual machines emulate an operational computing system, supporting an operating system, and perhaps one or more other applications as well. In some embodiments, each host includes a hypervisor that emulates virtual resources for the virtual machines using physical resources that are abstracted from view of the virtual machines. The hypervisor also provides proper isolation between the virtual machines. Thus, from the perspective of any given virtual machine, the hypervisor provides the illusion that the virtual machine is interfacing with a physical resource, even though the virtual machine only interfaces with the appearance (e.g., a virtual resource) of a physical resource. Examples of physical resources including processing capacity, memory, disk space, network bandwidth, media drives, and so forth.

The present disclosure may be embodied in other specific forms without departing from its spirit or essential characteristics. The described embodiments are to be considered in all respects only as illustrative and not restrictive. The scope of the disclosure is, therefore, indicated by the appended claims rather than by the foregoing description. All changes which come within the meaning and range of equivalency of the claims are to be embraced within their scope.

While various aspects and embodiments have been disclosed herein, other aspects and embodiments are contemplated. The various aspects and embodiments disclosed herein are for purposes of illustration and are not intended to be limiting. Additionally, the words "including," "having," and variants thereof (e.g., "includes" and "has") as used herein, including the claims, shall be open ended and have the same meaning as the word "comprising" and variants thereof (e.g., "comprise" and "comprises").

The invention claimed is:

1. A method, implemented at a computer system that includes at least one processor, for generating and playing back a personalized state song representing a target state of a user, the method comprising:
   accessing one or more portions of biometric data corresponding to one or more bodily systems of the user;
   encoding the one or more portions of biometric data into data structures that are configured for modeling using an algorithm that is specific to the user;
   modeling the encoded biometric data to identify one or more specified patterns, found in rhythmic recurrences of at least one of frequencies and amplitudes, or repeated highs and lows, in the encoded biometric data, the identified patterns being used to generate a personalized algorithm that corresponds with the identified patterns unique to the user, the personalized algorithm comprising lines of sound which sonify the encoded biometric data;
   synthesizing a state song using the personalized algorithm, the state song representing a specific biometric state for at least one of the bodily systems, using the lines of sound to create endogenous music; and
   playing back the state song to the user to induce the user to the specific biometric state.

2. The method of claim 1, wherein modeling the encoded biometric data further comprises:
   identifying one or more relationships between different types of biometric data;
   wherein generating the personalized algorithm implements as input the identified relationships between the different types of biometric data.

3. The method of claim 2, wherein the different types of biometric data are received from specialized biomedical devices.

4. The method of claim 1, wherein the encoding is performed at a transcoding engine that includes an encoding layer configured to encode the biometric data into musical elements by mapping the biometric data according to at least one of sampling rate, filters, reverb or compression.

5. The method of claim 4, wherein a default mapping is established for each type of biometric data.

6. The method of claim 1, wherein the encoding is performed at a transcoding engine that includes an encoding layer configured to encode the biometric data into musical elements by mapping different types of the biometric data to different instruments or sounds.

7. The method of claim 6, wherein an artificial intelligence engine is implemented to learn musical patterns that make music acoustically desirable, and wherein the learned musical patterns are used when mapping different types of biometric data to the instruments or sounds.

8. The method of claim 1, wherein the state song is played back to the user in reaction to the user reaching a specified, undesirable biometric state.

9. The method of claim 1, wherein the state song is played back to the user proactively to prevent the user from reaching a specified, undesirable biometric state.

10. The method of claim 1, further comprising rendering a graph that is an isomorphic representation of the one or more portions of biometric data to create a digital twin of the user.

11. A computer system, comprising:
    one or more processors;
    system memory;
    a data accessing module configured to access one or more portions of biometric data representing operations of one or more bodily systems of a user;
    an encoding layer configured to encode the one or more portions of biometric data, wherein encoding prepares the data for modeling at a modeling layer;
    the modeling layer configured to identify one or more specified patterns, found in rhythmic recurrences of at least one of frequencies and amplitudes, or repeated highs and lows, in the encoded biometric data, wherein the identified patterns are used to generate a personalized algorithm that corresponds with the identified patterns unique to the user, the personalized algorithm comprising lines of sound which sonify the encoded biometric data;
    a synthesis layer that uses the personalized algorithm to synthesize a state song representing a specific biometric state for at least one of the bodily systems, using the lines of sound to create endogenous music; and
    a playback module that plays the synthesized state song back to the user to induce the user to the specific biometric state.

12. The computer system of claim 11, wherein identifying specified patterns in the encoded biometric data further comprises identifying noise in the biometric data.

13. The computer system of claim 11, further comprising a filtering layer that is configured to filter at least a portion of identified noise in the biometric data.

14. The computer system of claim 11, further comprising an artificial intelligence layer configured to examine one or more existing songs and provide one or more musical elements as input to the synthesis layer indicating how the state song is to be generated.

15. The computer system of claim 11, further comprising a sharing layer configured to provide the synthesized state song to one or more other users.

16. The computer system of claim 11, further comprising a graphical user interface (GUI) that allows users to specify how biometric data from different biological systems is to be mapped to, instruments, or sounds.

17. A method, implemented at a computer system that includes at least one processor, for controlling state dependent behaviors of a user, the method comprising:
obtaining biometric data from one or more data capture devices placed in contact with the user, the biometric data comprising different types of biometric data;
associating at least some of the obtained biometric data with a plurality of specified instruments or sounds, each instrument or sound being mapped to a different type of biometric data;
compiling at least some of the instruments or sounds into a composition or song of endogenous music arranged to represent a targeted state; and
providing the composition or song back to the user to induce the user to the targeted state.

18. The method of claim 17, wherein endogenous music is combined with exogenous music.

19. The method of claim 17, further comprising providing one or more genre filters for the obtained biometric data.

20. The method of claim 17, wherein the biometric data is moved to a service oriented architecture (SOA) that provides one or more services including distributed processing and distributed storage.

* * * * *